(12) United States Patent
Juez et al.

(10) Patent No.: US 9,581,557 B2
(45) Date of Patent: Feb. 28, 2017

(54) USE OF RADIOFREQUENCY WAVE ABSORBING MARKETS FOR THE AUTHENTICATION OF SECURITY DOCUMENTS

(75) Inventors: Vicente Garcia Juez, Madrid (ES); Jose Francisco Fernandez Lozano, Madrid (ES); Javier Gamo Aranda, Madrid (ES); Miguel Angel Rodriguez Barbero, Madrid (ES); Juan José Romero Fanego, Madrid (ES)

(73) Assignees: Fabrica Nacional De Moneda Y Timbre-Real Casa De La Moneda (ES); Consejo Superior De Investigaciones Cientificas, C.S.I.C. (ES)

( * ) Notice: Subject to any disclaimer, the term of this patent is extended or adjusted under 35 U.S.C. 154(b) by 372 days.

(21) Appl. No.: 14/009,293

(22) PCT Filed: Mar. 30, 2012

(86) PCT No.: PCT/EP2012/055806
§ 371 (c)(1),
(2), (4) Date: Jul. 24, 2014

(87) PCT Pub. No.: WO2012/131045
PCT Pub. Date: Oct. 4, 2012

(65) Prior Publication Data
US 2014/0375424 A1    Dec. 25, 2014

Related U.S. Application Data

(60) Provisional application No. 61/493,078, filed on Jun. 3, 2011.

(30) Foreign Application Priority Data

Apr. 1, 2011 (EP) .................................... 11382093

(51) Int. Cl.
*G01N 23/06* (2006.01)
*B41M 3/14* (2006.01)
(Continued)

(52) U.S. Cl.
CPC ............. *G01N 23/06* (2013.01); *B41M 3/144* (2013.01); *B42D 25/00* (2014.10); *B42D 25/29* (2014.10);
(Continued)

(58) Field of Classification Search
CPC .......... B42D 25/29; B42D 25/00; G07D 7/06; G07D 7/122; B41M 3/14; B82Y 30/00; G01J 3/44; G06K 9/00577; G01N 21/658
(Continued)

(56) References Cited

U.S. PATENT DOCUMENTS

| 6,692,031 B2 * | 2/2004 | McGrew | B41M 3/144 283/57 |
| 2004/0001568 A1 * | 1/2004 | Impson | G06Q 10/08 378/60 |

(Continued)

FOREIGN PATENT DOCUMENTS

| CN | 1528840 A | 9/2004 |
| CN | 101055916 A | 10/2007 |

(Continued)

OTHER PUBLICATIONS

English translation; Chinese Application No. CN1528840A; 5 pages.
English translation; Chinese Application No. CN101100315B; 4 pages.
English translation equivalent; Chinese Application No. CN101055916; 15 pages.
Zhang et al., 11 pages.

*Primary Examiner* — Mirza Alam
(74) *Attorney, Agent, or Firm* — Blank Rome LLP

(57) ABSTRACT

The present invention relates to the use of non-deactivatable security compositions comprising the combination of at least
(Continued)

two types of particles of oxide materials, where said particles have a different size and/or morphology, and where the inorganic oxide materials have at least one transition metal or one lanthanide element, and radiofrequency wave absorption properties. The invention also relates to security articles, documents or elements incorporating these compositions, as well as to a method and to a system for detection thereof.

15 Claims, 2 Drawing Sheets

(51) Int. Cl.
| | | |
|---|---|---|
| C09D 7/12 | (2006.01) | |
| G07D 7/12 | (2016.01) | |
| G07D 7/06 | (2006.01) | |
| B42D 25/29 | (2014.01) | |
| B42D 25/355 | (2014.01) | |
| B42D 25/00 | (2014.01) | |
| G06K 7/10 | (2006.01) | |

(52) U.S. Cl.
CPC ......... *B42D 25/355* (2014.10); *C09D 7/1216* (2013.01); *C09D 7/1291* (2013.01); *G06K 7/10009* (2013.01); *G07D 7/06* (2013.01); *G07D 7/122* (2013.01); *B42D 2033/20* (2013.01); *B42D 2033/32* (2013.01)

(58) Field of Classification Search
USPC .................................. 340/5.86; 704/273, 201
See application file for complete search history.

(56) References Cited

U.S. PATENT DOCUMENTS

| | | | |
|---|---|---|---|
| 2004/0111624 A1* | 6/2004 | Odagawa | G06K 9/0002 713/185 |
| 2004/0177789 A1 | 9/2004 | Heider et al. | |
| 2007/0005367 A1* | 1/2007 | DeJean | G06K 19/086 704/273 |
| 2007/0165209 A1* | 7/2007 | Natan | G01J 3/44 356/71 |
| 2007/0178295 A1* | 8/2007 | Haas | B32B 5/18 428/304.4 |
| 2008/0276817 A1* | 11/2008 | Hinch | C09D 11/36 101/491 |
| 2010/0024681 A1 | 2/2010 | Krietsch et al. | |
| 2010/0050901 A1* | 3/2010 | Biris | B42D 25/29 106/31.14 |
| 2011/0018252 A1 | 1/2011 | Petry et al. | |

FOREIGN PATENT DOCUMENTS

| | | |
|---|---|---|
| CN | 101100315 A | 1/2008 |
| DE | 4114732 A1 | 11/1992 |
| ES | 8204666 | 8/1982 |
| GB | 2438196 | 5/2008 |
| JP | 2003248790 A | 9/2003 |
| WO | WO 96/05522 A2 | 2/1996 |
| WO | 2007/079453 A2 | 7/2007 |

* cited by examiner

USE OF RADIOFREQUENCY WAVE ABSORBING MARKETS FOR THE AUTHENTICATION OF SECURITY DOCUMENTS

REFERENCE TO RELATED APPLICATION

The present application is a National Stage of International Patent Application No. PCT/EP2012/055806, filed Mar. 30, 2012, published on Oct. 4, 2012, as WO 2012/131045 A1, which claims the benefit of EP 11382093.0, filed Apr. 1, 2011 and U.S. Provisional Application No. 61/493,078, filed Jun. 3, 2011, whose disclosures are hereby incorporated by reference in their entirety into the present disclosure.

FIELD OF THE INVENTION

The present invention relates to non-deactivatable security compositions which can be used as carriers of authentication or anti-forgery features in security documents or articles.

BACKGROUND OF THE INVENTION

A security document or security paper can be defined as that which has particular features assuring its origin and, therefore, its authenticity. Those security documents include travel and identification documents, bank notes, checks, stamps and stamped paper, labels or tickets, among many others.

A security element can be defined as that which is integrated in the security document in its pulp (such as, for example, the security thread, security fibers, watermarks, tactile effects or other elements commonly used) or on its surface (such as, for example, holograms added in different notes and credit cards, security inks, plastic films or other elements which are commonly used), randomly distributed or fixed in specific positions of the document and conferring security features to the document containing it, these features being able to greatly vary provided that their purpose is to hinder the forgery of security documents or to facilitate their authentication.

The use of different security elements has expanded in recent years as is proven by the number of patents in this field.

Some of these elements are detectable directly by humans, whereas other security elements incorporated in the documents require the use of special tools for their detection. A clear example is the luminescent substances or dyes existing in various security documents which require the use of a special light (for example ultraviolet light) for observation.

The use of luminescent substances or dyes for certifying authenticity in security documents has been known for a long time now (such as, for example, German patent number 449133 from the year 1925).

The use of luminescent substances or dyes of this type for certifying the authenticity of documents presents several drawbacks. One of the greatest drawbacks is the limited amount of optical transitions (absorptions and emissions) with properties suited for this application. As described in U.S. Pat. No. 4,451,530, a security dye or substance must show optical emissions centered in a well-defined frequency and preferably in a narrow band. These properties are present in the family of so-called rare earth elements (lanthanides with a valence 3+), as shown in the book "An introduction to the Optical Spectroscopy of Inorganic Solids" (J. García Solé, L. E. Bausá, and D. Jaque, © 2005 John Wiley & Sons, Ltd ISBNs: 0-470-86885-6 (HB); 0-470-86886-4 (PB)). The optical properties of all the rare earth elements are tabulated in Dieke's diagram [Dieke, G. H., *Spectra and Energy Levels of Rare Earth Ions in Crystals*, Interscience, New York (1968)], such that they are known and limited, a feature which involves a high risk of vulnerability and limits the scope of application because they cannot be used as a coded element.

The use of materials with a certain magnetic response for marking goods is also well known. One of the possible applications is the use of soft magnetic materials presenting hysteresis cycles with a large Barkhausen discontinuity, such as those described in patent U.S. Pat. No. 7,336,215 B2. In this case they are wires made of a soft magnetic material, generally based on metals or metal alloys, with diameters of several tenths of a millimeter.

Anti-theft markers based on magnetic responses are generally fairly large, having sizes of several millimeters or centimeters, and are coupled in different ways to the products to be protected. U.S. Pat. No. 4,484,184 describes one of these anti-theft markers based on the use of soft magnetic materials with a particular response to an oscillating magnetic field at a determined frequency. This marker has a size of several millimeters, making its presence detectable to the naked eye. In addition, in general these anti-theft markers usually have a performance that relies heavily upon their shape, such that when they are deformed thy may lose their functionality.

Anti-theft magnetic marking systems are based on producing electromagnetic fields with a determined frequency in response to an interrogating alternating electromagnetic field, which allows remote detection in a simple manner. These markers can be activated and deactivated by applying a suitable magnetic field for that purpose. This feature is very useful for marking products in a shop and preventing theft but limits its use as a marker in a security document.

There are different patents relating to systems for detection for security elements operating in the microwave range. In this sense, patent WO 9927502 describes a portable-sized microwave detector for particles acting as electric dipoles. The device measures the reflection and transmission of a radiofrequency wave striking the document containing the aforementioned particles, and it performs different operations with the measurements obtained, comparing with values which require being stored previously as reference values, in order to determine the authenticity of the document. However this system for detection is not robust enough and can give false positives.

BRIEF DESCRIPTION OF THE INVENTION

The object of the present invention is therefore to provide a new type of codifiable and non-deactivatable security markers not perceived by the naked eye, as well as a robust system and method for detection thereof.

The inventors have found that the combination of at least two types of particles of inorganic oxide materials having a different size and/or morphology, and where the inorganic oxide materials have at least one transition metal or one lanthanide element, provides stable and non-deactivatable security systems with a defined capacity for absorbing electromagnetic waves at radiofrequencies. Since the absorption properties vary with the size and the morphology of the particles, the security system will have as many signals as it has types of particles of a different size and/or morphology. This allows increasing the reliability of the security systems because they will have at least two specific absorption bands, as well as hindering forgers from identifying the security system because it would be necessary to elucidate the chemical composition and the specific size and/or morphology of each of the types of particles used. Furthermore, taking into account the high number of variables defining the absorption properties of the combination, this system gives rise to a virtually unlimited number of unique security markers.

Moreover, since radiofrequency (RF) radiation has higher penetration power than other kind of radiations such as UV radiation, using inorganic oxide materials having radiofrequency wave absorption properties would allow detecting in more accurate manner markers inside of security documents. Radiofrequency could be detected by simple non-contact system and could be used from up to several meters away.

As a consequence, in one aspect the invention relates to a security element, article or document comprising a composition comprising the combination of at least two types of particles of inorganic oxide materials, where each of the at least two types of particles has a different size and/or morphology, and where the inorganic oxide materials have at least one transition metal or one lanthanide element.

The security composition of the invention has RF wave absorption properties and can therefore be used to determine the authenticity of security articles or documents.

In a second aspect, the invention relates to the use of the security compositions of the invention for preparing or marking a security article or document.

In another aspect, the invention relates to a security document, article or element comprising the security composition of the invention.

In another aspect, the invention relates to a method for authenticating a security document or article which comprises measuring the RF absorption of a composition comprising the combination of at least two types of particles of inorganic oxide materials, where each of the at least two types of particles has a different size and/or morphology, and where the inorganic oxide materials have at least one transition metal or one lanthanide element.

In another aspect, the invention relates to an apparatus for detecting the presence of the security composition of the invention in a security document or article.

DESCRIPTION OF THE DRAWINGS

For the purpose of aiding to better understand the features of the invention according to a preferred practical embodiment thereof, the following description of a set of drawings is provided, wherein the following has been depicted in an illustrative manner.

DETAILED DESCRIPTION OF THE INVENTION

Compositions

Figure 1:
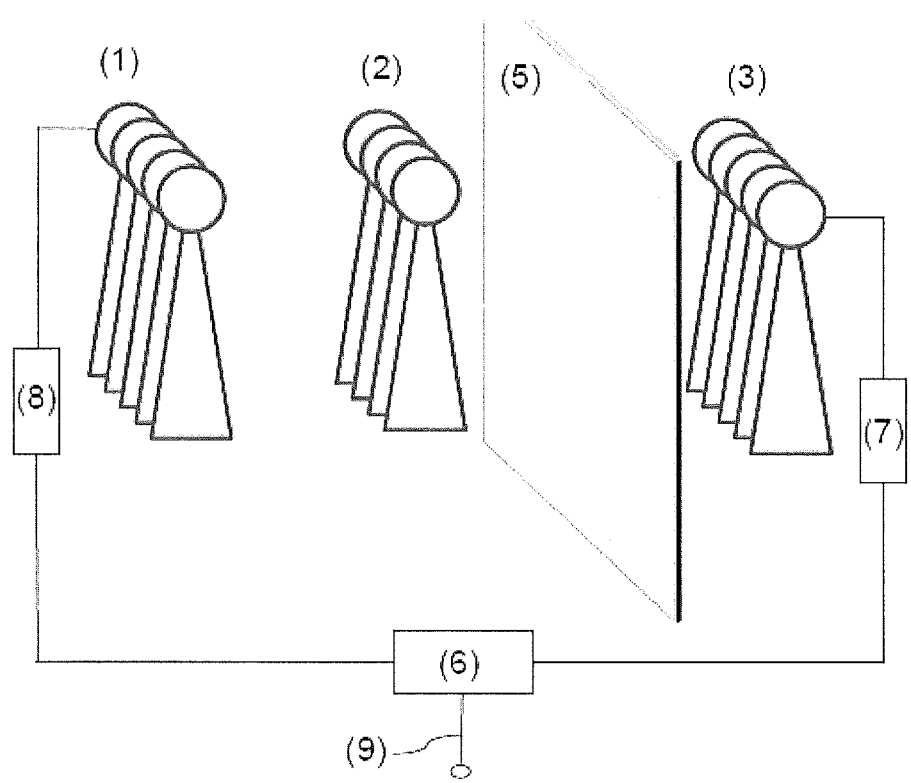
FIG. 1 shows a schematic depiction of the system for detection object of the invention.

The present invention relates to a security composition comprising the combination of at least two types of particles of inorganic oxide materials, where each of the at least two types of particles has a different size and/or morphology, and where the inorganic oxide materials have at least one transition metal or one lanthanide element, and radiofrequency wave absorption properties.

The term "security composition" or "composition of the invention" relates to a composition comprising the combination of at least two types of particles of inorganic oxide materials, where each of the at least two types of particles has a different size and/or morphology, and where the inorganic oxide materials have at least one transition metal or one lanthanide element, and presents radiofrequency wave absorption properties.

The term "combination" in the present application relates to a physical mixture of the at least two types of particles.

According to the present invention the term "oxide material" relates to any inorganic chemical compound containing one or several oxygen atoms in a −2 oxidation state, and other elements.

According to a particular embodiment, the at least two types of particles of inorganic oxide materials have the same chemical composition and, therefore, they differ only in the size and/or morphology of said particles.

According to another embodiment, each type of particles of the composition has a different chemical composition.

In a particular embodiment of the invention, the security composition comprises two, three or four types of particles having a different size and/or morphology.

The term "radiofrequency" (RF) relates to electromagnetic waves in the range of from about 3 KHz to about 300 GHz.

The particles of oxide materials forming the security composition of the invention have RF wave absorption properties defined preferably between about 3 KHz and about 300 GHz. According to a particular embodiment, they absorb electromagnetic waves at radiofrequency between about 1 MHz and about 100 GHz, preferably between about 1 and 100 GHz.

In a particular embodiment, the security composition of the invention has at least two emission bands defined at specific frequencies.

The oxide materials constituting the particles of the composition of the invention preferably have at least one transition metal and/or one lanthanide element in their composition.

The transition metals, or transition elements, are those having electrons housed in the d-orbital, such as, for example, Sc, Ti, V, Cr, Mn, Fe, Co, Ni, Cu, Zn, Y, Zr, Nb, Mo, Ru, Rh, Pd, Ag, Cd, Hf, Ta, W, Re, Os, Ir, Pt or Au. According to a particular embodiment of the invention, the transition metal is selected from Co, Fe, Zn, V, Nb, Cr, Ni, Pt and Ti.

The lanthanide elements are those forming part of period 6 of the periodic table and including from atomic number 57 to 71, i.e., Ln, Ce, Pr, Nd, Pm, Sm, Eu, Gd, Tb, Dy, Ho, Er, Tm, Yb and Lu. According to a particular embodiment of the invention, the lanthanide element is selected from Sm, Nd, Ho, Ce and Pr.

Previously synthesized oxide materials having well-defined RF wave absorption properties can be used in the present invention. The oxide materials used in the invention preferably have crystalline structures. In a particular embodiment, the oxide materials used in the present invention are selected independently from wurtzite, spinel, ferrite, garnet or perovskite-type structures.

In a particular embodiment, the oxide materials contain at least one transition metal and/or one lanthanide element in their composition and have a crystalline structure, preferably of the wurtzite, spinel, ferrite, garnet or perovskite-type.

Materials with a wurtzite structure relates to those having general chemical formula MO, where M represents a transition metal, such as, for example, ZnO, FeO, TiO.

Materials with a spinel structure relates to those having general chemical formula $AB_2O_4$, where A represents a divalent element, such as, for example, alkaline earth elements, lanthanides or transition metals (e.g. Mg, F, Mn, Zn) and B represents a trivalent element, such as, for example, the elements of group 13 of the periodic table, transition metals or rare earth elements (e.g. Al, Cr, Fe). Particular examples of materials of this type are $CoFe_2O_4$, $FeCr_2O_4$.

Materials with a ferrite-type structure relates to those having general chemical formula $(XO)_m(Y_2O_3)_n$, where X is a divalent element such as, for example, an alkaline earth element, a transition metal or a rare earth element or mixtures thereof; Y is a trivalent element, such as, for example, the elements of group 13 of the periodic table, transition metals or rare earth elements (e.g. Fe, Al); and m and n can have any integer values, preferably between 1 and 20. $BaCoZnFe_{16}O_{27}$ can be mentioned as an example of materials of this type.

Materials with a garnet-type structure relates to those having general formula $A_3B_2(DO_4)_3$, where A represents alkaline elements, alkaline earth elements, transition metals or lanthanides or mixtures thereof; and B represents transition metals, lanthanides or silicon or mixtures thereof; and D represents silicon, vanadium, aluminum or iron or mixtures thereof. $(Bi_{0.75}Ca_{1.2}Y_{1.05})(V_{0.6}Fe_{4.4})O_{12}$ can be mentioned as a possible example of materials of this type.

Materials with a perovskite-type structure relates to those having general formula $ABO_3$, where A represents alkaline elements, alkaline earth elements or lanthanides and B represents Si, Ge, Sn, I or transition metals. A possible example of materials of this type are those forming part of the solid solution $(1-x)NaNbO_3 \cdot xPbTiO_3$.

The particles of these oxide materials can be synthesized by different conventional methods known by experts in processes and materials of this type, particularly by ceramic, mechanochemical, chemical or electrochemical methods or by physical or chemical vapor deposition techniques. The morphology and the size of the particles of the invention can be selected during the synthesis process itself, using for example suitable surfactants in the processes of manufacturing by chemical methods, or by means of performing controlled milling processes to reduce the particle size from massive materials. These oxide materials will be prepared in the form of particles, with isotropic or anisotropic morphologies.

A particular embodiment of this invention comprises the use of sub-micron sized particles of oxide materials, particularly nanometric sized. In this case, the particles of oxide materials are supported and anchored on larger sized particles, using to that end for example the techniques described in patent application WO 2010/010220, or embedded in other materials that do not present electromagnetic wave absorption in the region of interest.

In the context of the present invention, the term "particle" relates to a structure the mean size of which is micrometric or nanometric, preferably a mean size comprised between 1 nm and 50 μm. The particles of the invention preferably have a size between 1 μm and 50 μm; whereas when the particles present a nanometric mean size, i.e., between 1 and 1000 nm, such particles form aggregates the mean size of which is between 1 μm and 50 μm.

More preferably, the particles, or the particle aggregate, of oxide materials of the present invention have an average size between 1 and 45 micrometers, preferably between 2 and 20 micrometers. Alternatively, these particles could be formed by combinations of distinct smaller-sized particles provided that the size of the aggregate of said combinations is within the range of sizes described above.

Preferably, the variation in the particle size distribution is less than 20% the mean particle size. This size variation assures that the absorption for a determined frequency is characterized by an intensity and bandwidth specific for each oxide material making up the security composition of the invention.

In a particular embodiment, the particles of oxide materials have morphologies selected independently between spherical, pseudospherical, tapered, laminar, pseudolaminar, fibrillar, polyhedral and platelets.

According to one embodiment of the invention, the security element comprises two types of particles at a ratio between 1:1 and 20:1 by weight, preferably between 1:1 and 10:1, more preferably between 1:1 and 5:1 or between 1:1 and 3:1 by weight.

The oxide materials forming the security element are characterized by presenting well-defined RF wave absorption properties which are determined by their composition and by their morphology and size.

Oxide materials that present RF wave absorption properties are well known in the state of the art. Nevertheless, whether an oxide material presents RF wave absorption properties can be readily determined by appropriate measurements using different frequency-selective equipments, known to those skilled in the art, such as specifically designed antennas connected to frequency analyzers or oscilloscopes.

The frequencies at which these oxide materials present electromagnetic fieldabsorption are determined by their particular composition and can be modified by means of composition changes, for example, adding different amounts of other ions. Thus, for example, in the case of the family of the aforementioned pervoskites, $(1-x)NaNbO_3 \cdot xPbTiO_3$, the absorption frequency can be modified from 8.8 GHz to 9.2 GHz by changing the value of x between 0.15 and 0.24.

Two oxide materials with the same composition and different particle size have different absorption properties. Thus, for example, in the case of ferrite $BaCoZnFe_{16}O_{27}$, there are variations in the frequency at which the absorption occurs from 14.5 GHz for particles of 3 microns down to 11.5 GHz for particles of 320 nm.

Likewise, two oxide materials having particles of a different morphology will also present different electromagnetic wave absorptions. Thus, for example, in the case of ZnO, the electromagnetic wave absorption frequency drops from 16 to 12 GHz when instead of using microparticles nanotetrapods are used.

An additional aspect of the invention relates to the use of a composition comprising a combination of at least two types of particles of inorganic oxide materials, where each of the at least two types of particles has a different size and/or morphology, and where the inorganic oxide materials have at least one transition metal or one lanthanide element, and RF wave absorption properties as defined above, for preparing or marking a security document or article.

The security compositions of the invention comprise a combination of at least two inorganic oxide materials, each one including at least one transition metal or lanthanide element on its composition, with different size and/or morphology and, therefore, with distinct absorption properties. The security compositions will be formed either by particles with a different size, or by particles with a different morphology, or by particles with a different size and morphology, giving rise to a targeted, defined and reproducible mixture. This combination of particles of oxide materials constitutes a codifiable security marker. Thus, for example, two particles of oxide materials with a different morphology or size will have different absorption properties, even though they are formed by oxide materials with the same chemical composition. This increases the complexity of the security marker because it is characterized both by the composition thereof and by the size and/or the morphology of the particles forming it.

An example of a security composition would comprise particles of two or more different oxide materials with different particle sizes for each of them. A particular embodiment of this example would be a 50% by weight mixture of spinel $CoFe_2O_4$ with a particle size of 2 microns with garnet $(Bi_{0.75}Ca_{1.2}Y_{1.05})(V_{0.6}Fe_{4.4})O_{12}$ with a particle size of 3 microns. This security composition shows two distinct absorption bands.

Another example of a security composition would comprise a combination of two or more types of particles of one and the same oxide material with a different particle size but the same morphology for all of them. A particular embodiment of this example would be a combination of spherical particles of $BaCoZnFe_{16}O_{27}$ with sizes of 3 and 0.3 microns.

Another example of a security composition would comprise the combination of two or more types of particles of one and the same oxide material with a different morphology and the same particle size according to the largest dimension thereof. A particular embodiment of this example would be a combination of spherical particles of $BaCoZnFe_{16}O_{27}$ with sizes of 3 microns and tapered particles of 3 microns in length and 1 micron in diameter of $BaCoZnFe_{16}O_{27}$.

Another example of a security composition would comprise the combination of particles of one or more particular oxide materials with a defined morphology and particle size with particles of another oxide material with two or more defined particle sizes and the same morphology, A possible embodiment of this example would be a combination of 30% by weight of spherical particles of 2 microns in diameter of spinel $CoFe_2O_4$ with 30% by weight of ferrite $BaCoZnFe_{16}O_{27}$ with a size of 3 microns and spherical morphology and 40% by weight of this same ferrite $BaCoZnFe_{16}O_{27}$ with a size of 0.3 microns and spherical morphology. Three distinct absorption bands are thus obtained.

Security Documents, Articles and Elements

In one aspect the invention relates to a security element comprising the composition of the invention as defined above.

According to the present invention, the term security element relates to an element which is integrated in a security document or article for authentication purposes. The security element can be integrated in the security article or document in its pulp (such as, for example, security paper, paper pulp, security threads, security fibers, watermarks, tactile effects, cellulose strips, planchettes or other elements commonly used) or on its surface (such as, for example, holograms added in different notes and credit cards, security inks, plastic films or other elements which are commonly used). It can be randomly distributed or fixed in specific positions of the document or article and confers security features to the document or article containing it, these features being able to greatly vary provided that their purpose is to hinder the forgery of the security documents or articles or to facilitate their authentication.

According to a particular embodiment, the security element is selected, for example, from security paper, paper pulp, security threads, security fibers, security inks, watermarks, tactile effects, cellulose strips, planchettes, holograms, security dyes or substances, plastic films, polymer substrates.

These security elements can be prepared from the security compositions defined above following the standard methods known by the person skilled in the art.

Additionally, these security elements can be used for marking security articles or documents.

In another aspect the invention also relates to a security article or document comprising a security composition as defined above.

According to the present invention, the term security article or document relates to that having particular features assuring its origin and, therefore, its authenticity. Those security articles or documents include identification documents, such as identification cards, passports, passes and the like, and value documents, such as notes, checks, stamps, certificates and the like.

The security article or document is preferably selected from security paper, identification documents, bank notes, checks, stamps and stamped paper, labels and tickets. More preferably, it is security paper.

The security composition of the invention can be incorporated in the security article or document:
 (i) during the manufacture of the material used for making said article or document; or
 (ii) as part of an additive which is added to said article or document; or
 (iii) on the surface of said article or document.

The security composition of the invention can be added to the paper pulp of the security documents as dry filler, forming part of paper pulp itself. This security composition can also be incorporated on the surface of the document as a hologram or security thread visible against the light, or forming part of the sizing or lacquering. The security composition can be incorporated into the inks used for printing the security document, being able to form an unnoticeable part of images, figures, legends, barcodes or tactile marking elements.

The particle sizes defined in the invention assure their incorporation and permanence in the paper. The security document or article is thus provided with the code corresponding to the chosen combination of particles.

The combinations of particles of the invention have a particle size described and characterized for not being detectable to the naked eye when they are integrated in the security document or article. In a particular embodiment, the percentage of the security composition incorporated in the security document or article is less than 5% by weight, preferably less than 1% by weight, and greater than 0.005% by weight of the total weight of the security document or article. This low concentration hinders identifying the composition by techniques used such as chemical analysis, X-ray diffraction, spectroscopic techniques or the like. Nevertheless, the identification of the composition does not itself represent the security marker because the specific response is achieved by the set of elements combined in the security element, an aspect which makes each one of them unique and therefore the bearer of a code.

The number of different security markers increases with the number of different absorbent oxide materials used and it can be considered as virtually unlimited. This allows generating coded security markers, such that a determined security marker corresponds to documents that have been created at a certain time or for a determined value or particular purpose or by a determined organism, therefore making the security documents traceable and further increasing the security thereof.

These security compositions are always active, it being impossible for a security composition to not show the RF radiation absorption bands which characterize them by the application of other electromagnetic waves or other external fields whether they are electrical, luminous magnetic or thermal fields. It is therefore impossible for a security document to be mistaken with a forgery because it does not present the features corresponding to the security element. Likewise, the materials comprised in the security compositions cannot modify their response to electromagnetic absorption without destroying the security document which they are indissolubly a part of, so the security compositions are characterized by being permanent and non-deactivatable.

The particles forming the security compositions of the invention are formed by oxide materials, where the inorganic oxide materials have at least one transition metal or one lanthanide element. These materials have the great advantage of being very stable, generally not being sensitive to oxidation or hydration processes. Nevertheless, the particles of oxide materials can occasionally be coated with layers of inert materials, such as the alumina, glass, silicates, or other oxide materials to protect them from the environment. Likewise, the particles could also be coated with polymers or other organic materials to improve their adherence to the fibers of the paper or to better incorporate them in the event that they form part of inks. Furthermore, using inorganic oxide materials having specific radiofrequency wave absorption properties allows detecting in more accurate manner markers inside of security documents.

The security compositions described in the present invention allow efficiently marking security articles or documents, presenting a secure coding system based on the intentional combination of particles of oxide materials showing absorption properties defined by their composition, morphology and size, giving rise to a virtually unlimited number of possible unique security markers. The security compositions described are permanent, non-deactivatable and have a coded response requiring the use of a system for detection designed for that purpose.

Method of Authentication

In another aspect, the invention relates to a method for determining the authenticity of a security document or article which comprises measuring the radiofrequency absorption of said security document or article to determine the presence of a composition comprising the combination of at least two types of particles of inorganic oxide materials, where each of the at least two types of particles has a different size and/or morphology, and where the inorganic oxide materials have at least one transition metal or one lanthanide element, and RF wave absorption properties.

In one embodiment, the invention relates to a method for determining the authenticity of a security document or article comprising a composition comprising the combination of at least two types of particles of inorganic oxide materials, where each of the at least two types of particles has a different size and/or morphology, and where the inorganic oxide materials have at least one transition metal or one lanthanide element, and radiofrequency wave absorption properties, which comprises:
(a) irradiating the security document or article with RF radiation; and
(b) determining the absorption of the RF radiation crossing the security document or article.

In a particular embodiment, the absorption of the RF radiation crossing the security document or article is determined by comparing the intensity of the RF radiation after crossing the security document or article with the intensity of the same RF radiation when it crosses a free space region.

Therefore, in one embodiment of the invention the method for determining the authenticity of a security document or article, as defined above, comprises:
(a) irradiating the security document or article with RF radiation;
(b) measuring the intensity of the RF radiation after crossing the security document or article;
(c) measuring the intensity of the RF radiation after crossing a free space region; and
(d) comparing the intensity of the signals of steps (b) and (c) to determine the absorption of the RF radiation crossing the security document or article.

The authenticity of the security document or article is verified if the absorption of the RF radiation crossing the security document or article is within established limits. Therefore, in a particular embodiment the method of the invention comprises an additional step of verifying the authenticity of the security document or article if the measured absorption is within established limits. Taking into account that the absorption of an ensemble of a definite number of individual elements corresponds to the sum of the absorption of all these elements, the method described here for the characterization of the security elements can be used to characterize simultaneously a definite number of security documents or articles. In this case, the absorption corresponding to an ensemble of X security documents or articles would correspond to X times the absorption of each individual item. In such a way, it is possible to determine the presence of a single forged element in an ensemble of elements without measuring each element individually.

According to one embodiment of the invention, the electromagnetic radiation used to irradiate the security document or article has a frequency between 3 KHz and 300 GHz.

According to another particular embodiment, the electromagnetic radiation absorption bands after crossing the security document or article represent a coding.

Detector

Another aspect of the present invention relates to an apparatus for detecting the presence of a security composition in a security document or article comprising:
a RF radiation transmitting antenna or antenna array (2),
a first RF radiation signal receiving antenna (3),
a second reference RF radiation receiving antenna (1),
where the first and second receiving antenna (1, 3) are arranged on either side of the transmitting antenna(s) (2) and where between the transmitting antenna (2) and the first receiving antenna (3) there are support means (4) for supporting the document (5) to be analyzed such that when the document (5) is in said support (4) in the operating mode, the document (5) is placed between the transmitting antenna(s) (2) and the first receiving antenna (3) and where the apparatus further has:

calculating means (6),
  first signal reading means (7) connected with the first receiving antenna (3) and suitable for delivering the value of the measured signal to the calculating means (6),
  second signal reading means (8) connected with the second receiving antenna (1) and suitable for delivering the measured reference value to the calculating means (6),
where the calculating means (6) have an output (9) and are suitable for determining if the difference of values between the value of the signal measured in the first receiving antenna (3) and the value of the reference signal measured in the second receiving antenna (1) is in a pre-established range, delivering said result in the output (9). The system for detection of the present invention allows detecting the RF absorption response of the security elements described above which have been effectively incorporated in the security article or document.

The system for detection of the present invention allows working at different frequencies in a very broad range. The apparatus of detection described above is used to determine the presence of the security elements described in the present invention, which is especially designed for said security elements. This apparatus is capable of determining the presence of the particular absorption bands characterizing each security element at determined frequencies. The apparatus (FIG. 1) comprises at least one transmitting antenna (2) which emits radiation at various frequencies, preferably in the range between 3 kHz and 300 GHz, and at least two receiving antennas (1, 3) which measure the intensity of radiation at the frequencies emitted by the transmitting antenna after crossing the security document or article containing the security element described, or after crossing a free space region. The comparison between the signals measured upon crossing the security document or article and a free space region provides the absorption values, which allow distinguishing the presence or absence of the specifically designed element and, therefore, the authenticity of the document or article. In a particular embodiment, the antennas forming each of the pairs of receiving antennas are arranged symmetrically with respect to the transmitting antennas. The receiving antennas are called signal receiving antennas (3) and reference antennas (1), respectively. The security document or article (5) containing the security element is placed between the transmitting antennas (2) and the receiving antennas called sample antennas (3). The space between the transmitting antennas (2) and the reference antennas (1) must remain free and cannot be altered.

Figure 2:
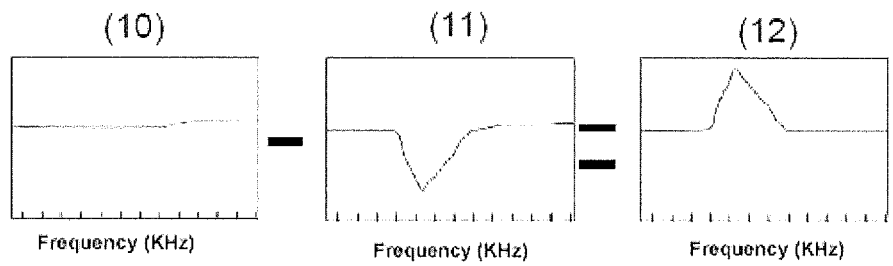
FIG. 2 shows three graphs which respectively show the signal detected in the reference antenna, in the sample antenna and the difference between both signals.

The final measurement results from the comparison of the electromagnetic field intensity measured in the signal receiving antennas (3) and the reference antennas (1). The difference between the measurements obtained with the antennas (3) and (1) is proportional to the absorption produced by the security element present in the security document or article, as depicted in FIG. 2. In this figure the spectrum shown in (10) corresponds to the measurement obtained in the reference antennas (1) and the one shown in (11) corresponds to the measurement obtained with the signal receiving antennas (3). When comparing both signals, for example by means of subtraction thereof, an absorption band corresponding to the coded signal of the security element shown in (12) is obtained. The system for detection of the security elements has extremely reliable results, minimizing the possibility of false positives or false rejections because the identification of the code provided by the security element does not depend on the position of the element to be measured with respect to the transmitting antenna.

Figure 3:
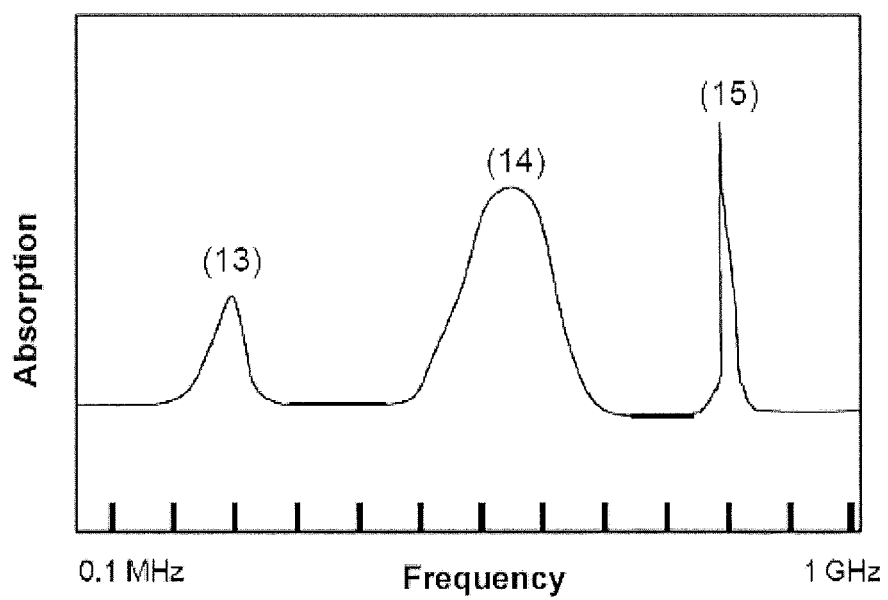
FIG. 3 shows an example of measurements using the system of the invention applied to a document with a marker which has three absorption peaks at three different frequencies.

The absorption measurements are performed in a broad frequency range, and the code of the security elements requires different absorption values in a range of specific frequencies, as shown in FIG. 3. This method is characterized by being more secure than the measurement of a single absorption band. The design of the system for detection allows it to be used for different security elements like those described in the present invention, without the need for prior calibration for each of them.

In one embodiment, the authenticity criterion is based on the authentication of the code of the security composition and it will be complied with if:
1. For each band (13, 14 and 15 in FIG. 3), a determined absorption value is obtained exclusively at frequencies defined for each particular security element. This condition means that there must be a determined amount of security element in the security document or article.
2. A determined relative coefficient between the absorption intensities or between the areas of the different absorption bands must be complied with.
3. The set of coefficients responds to the algorithm specific for each security element.

Thus, for example, as is schematically shown in FIG. 3, the absorption ratios 13/15, 14/15 and 13/14 must present defined values. These values can correspond to the absorption values at a determined frequency, or to the absorption values integrated in a determined frequency range, which can be equal or different for the different bands.

This validation system increases the robustness of the authentication against potential forgeries because if the intention is to trick the system using a material different from the original security element, even when said "false" material may present some response at any of the verification frequencies/bands, it will be virtually impossible for it to comply with all the authenticity criteria indicated above.

Therefore, the set of security compositions and the proposed system for detection allows in practice an almost unlimited increase of the number of coding operations that can be performed and detected, therefore being able to use security compositions which are not tabulated and the absorption features of which can be altered by means of modifying the physicochemical properties of the oxide materials forming them. General knowledge of the properties of the security compositions and their forgery is thus avoided, opening up a new pathway in security based on coding the security document, such that it can be unique for each type of document.

EXAMPLES

Example 1

Combination of Particles Consisted of 50% wt $La_{0.7}Sr_{0.3}MnO_{8\pm\delta}$ and 50% wt $La_{0.7}Sr_{0.3}Mn_{0.8}Co_{0.2}O_{8\pm\delta}$ as Security Markers Applied on the Surface of Security Paper to Print Legal Tender Notes Material:
a gravure printing machine manufactured by Panday-Graph,
a gravure cylinder manufactured by Ziraba,
natural cellular-based fibrous paper manufactured in a round paper machine in the FNMT, long-lasting varnish and crosslinker manufactured by Sicpa, and an aqueous dispersion of a combination of particles consisted of 50% wt $La_{0.7}Sr_{0.3}MnO_{8\pm\delta}$ and 50% wt $La_{0.7}Sr_{0.3}Mn_{0.8}CO_{0.2}O_{8\pm\delta}$ having an average particle size of 4 μm, where the composition present an absorption maximum at the frequency of 15.87 GHz and 11.31 GHz respectively.

Characteristics of the Installations and Materials Used:
Conditions of the Printing Machine on Each Side of the Paper:
  Unwinder Tension: 125 N
  Winder tension: 120 N
  Winding hardness: 14%
  Drying tunnel temperature: 145° C.
  Machine speed: 90 m/min
  Suction speed: 2500 rpm
  Blowing speed: 2400 rpm
  Residual moisture of the paper after drying: 6.1-6.8%
Conditions of the gravure cylinder
  Type of etching: chemical
  Lineature: 60 line/cm
  Cell depth: 54 microns
  Table: 910 mm
  Diameter: 200 mm
Conditions of the varnish and crosslinker:
  Commercial name of the varnish: Primer 803696W
  Commercial name of the crosslinker: First additive 370010
  Viscosity of the varnish after adding crosslinker: 20 s CP4
  Viscosity of the varnish for application: 18 s CP4
Characteristics of the paper:
  Fibrous composition: 100% cellulose
  Grammage: 90 g/m²
  Grammage after the varnishing process: 96 g/m²
  Thickness: 115 microns
  Bendtsen smoothness on the felt side: <700 ml/min
  Bendtsen smoothness on the fabric side: <800 ml/min
  Bendtsen porosity: <20 ml/min
  Bendtsen porosity after creasing: <140 ml/min
  Cobb value: 40-70 g/cm²
  Ash: <3%
  Opacity: 84%

Embodiment Method: Once the printing machine is started up to reach the established machine conditions, the gravure cylinder is placed, the reel of paper is placed on the unwinding shaft and the web of paper is distributed in the machine circuit, the varnish is mixed with the crosslinker in a proportion of 1.5% by weight of the latter over the former, under gentle stirring conditions in the actual 20 kg drum of varnish. 100 ml of the aqueous dispersion of the combination of particles as defined above are added to this mixture. Once the perfect dispersion of the components is assured, the content of the drum is pumped to the inkwell of the printing machine. The paper is positioned on the printing cylinder starting the application of the varnish on the entire width of the web of paper on one of the sides, controlling the final moisture of the paper, viscosity of the varnish and the machine conditions throughout the entire printing process. Once the paper is wound at the machine outlet, the reel is taken off the winder and is placed in the unwinder in the appropriate unwinding direction to print the varnish on the opposite side. After the process ends the reel is left at rest in a minimum development time of 24 hours at room temperature (23° C. and 50% RH).

Example 2

Combination of Particles Consisted of 70% wt of the Mixture Referred in the Example 1 and 30% wt of $Ni_{0.5}Zn_{0.5}Fe_2O_4$ Particles as Security Markers Applied in Security Paper Mass Intended for Printing Passports Material:
a round paper machine,
an aqueous dispersion of cellulose fibers suitably bleached and refined in previous production processes, and
an aqueous dispersion of a combination of particles consisted of 70% wt of the mixture referred in the example 1 and 30% wt of $Ni_{0.5}Zn_{0.5}Fe_2O_4$ particles with average particle of 1 μm where the last particle present an absorption maximum at the frequency of 4.7 GHz. Thus the mixture possesses 3 different absorption bands.

Embodiment Method: The aqueous dispersion of cellulose fibers along with different chemical products such as anti-foaming agents, charge retention agents, color fixing agents, mineral fillers (e.g. titanium dioxide or alumina silicate), pigment dyes, ion and pH regulators and dry resistance resins (e.g. carboxymethyl cellulose), form the base pulp for manufacturing paper with a consistency or concentration around 3% by weight with respect to the amount of water used with pH between 7 and 8. The aqueous dispersion of the combination of particles as defined above are functionalized to be cationic and to have the capacity to form covalent bonds with the oxygen atoms of the carboxyl groups of the cellulose fibers and placed in a 1000 kg dilution tank. The metering of the aqueous dispersion of the combination of particles towards the machine head ink first causes an electrostatic attraction between said combination of particles and the anionic fibers to later form the indicated covalent bond.

Wet resistance resin based on polyamide-epichlorohydrin which is also strongly cationic and has the possibility to form covalent bonds similar to that indicated is subsequently added to the paper pulp, and such bonds are formed with as many cellulose fibers are left with this option and it also forms such bonds with itself to form the polymer lattice necessary to give the paper the wet resistance level that is specified. This entire mass of cellulose fibers and chemical additives subsequently arrive from the machine head ink to the round shape where the layer of paper forming the final sheet of paper after the pressing, drying, gluing and subsequent drying and calendering processes is formed. The paper manufactured by these means is subsequently used for printing passports.

Example 3

Combination of Particles Consisted of 50% wt of $Fe_3O_4$ Nanowires and 50% wt of $Fe_3O_4$ Nanosheets as Security Markers Applied in Silk-Screen Printing Ink with an Iridescent Web in Security Paper for Security Labels Material:
a silk-screen printing machine manufactured by Stork,
a silk screen manufactured by Stork,
natural cellular-based fibrous paper manufactured in a round paper machine in the FNMT, iridescent ink, anti-foaming agent and crosslinker manufactured by Sicpa, and an aqueous dispersion of a combination of particles consisted of 50% wt of $Fe_3O_4$ nanowires with 30 nm in diameter and 500 nm in length and 50% wt of $Fe_3O_4$ nanosheets with 100 nm in side length where the composition present an absorption maximum at the frequency of 8.32 GHz and 10.24 GHz respectively.

Characteristics of the Installations and Materials Used:

Conditions of the printing machine on each side of the paper:
  Unwinder tension: 125 N
  Winder tension: 120 N
  Winding hardness: 14%
  Drying tunnel temperature: 145° C.
  Machine speed: 70 m/min
  Suction speed: 2500 rpm
  Blowing speed: 2400 rpm
  Residual moisture of the paper after drying: 6.5%
Conditions of the silk screen
  Reference: RSI900
  Development: 25⅜"
  Mesh: 105
  Open area: 15%
  Thickness: 105 microns
  Width: 910 mm
Conditions of the iridescent ink and additives:
  Commercial name of the ink: Silk-screen printing ink 5WR1241
  Commercial name of the anti-foaming agent: Additive 880775
  Commercial name of the crosslinker: Additive 370010
  Viscosity of the ink after adding crosslinker: 20 s CP4
  Viscosity of the printing ink: 18 s CP4
Main conditions of the paper:
  Fibrous composition: 100% cotton cellulose
  Grammage: 90 g/m$^2$
  Grammage after the varnishing process: 96 g/m$^2$
  Thickness: 115 microns
  Bendtsen smoothness on the felt side: <700 ml/min
  Bendtsen smoothness on the fabric side: <800 ml/min
  Bendtsen porosity: <20 ml/min
  Bendtsen porosity after creasing: <140 ml/min
  Cobb value: 40-70 g/cm$^2$
  Ash: <3%
  Opacity: 84%

Embodiment Method: Once the printing machine is started up to reach the established machine conditions, the silk screen is placed, the reel of paper is placed on the unwinding shaft and the web of paper is distributed in the machine circuit, the ink is mixed with the crosslinker in a proportion of 1.5% by weight of the latter over the former, under gentle stirring conditions in the actual 20 kg drum of ink. 100 ml of the aqueous dispersion of the combination of particles as defined above and anti-foaming agent are added to this mixture as needed should foam occur. Once the perfect dispersion of the components is assured, the content of the drum is pumped to the inkwell of the printing machine. The paper is positioned on the printing silk screen starting the printing of the ink through the holes of the screen according to the graphic design established therein on one of the sides, controlling the final moisture of the paper, viscosity of the ink and the machine conditions throughout the entire printing process.

Example 4

Combination of Particles Consisted of 25% wt of $Fe_3O_4$ Nanowires, 25% wt of $Fe_3O_4$ Nanosheets, 25% wt of $\beta\alpha$-$MnO_2$ Nanowires and 25% wt of $\beta$-$MnO_2$ Microrods as Security Markers Applied on the Surface of the Security Paper Intended for Printing Passports Material:

A round paper machine and
an aqueous dispersion of cellulose fibers suitably bleached and refined in previous production processes,
an aqueous dispersion of a combination of particles consisted of 25% wt of $Fe_3O_4$ nanowires with 30 nm in diameter and 500 nm in length, 25% wt of $Fe_3O_4$ nanosheets with 100 nm in side length, 25% wt of $\beta\alpha$-$MnO_2$ nanowires with 50 nm in diameter and 3 μm in length and 25% wt of $\beta$-$MnO_2$ microrods with 4 μm in diameter and 8 μm in length where the composition present an absorption maximum at the frequency of 8.32 GHz, 10.24 GHz, 5.3 GHz and 1.4 GHz respectively.

Embodiment Method: The aqueous dispersion of cellulose fibers along with different chemical products such as anti-foaming agents, charge retention agents, color fixing agents, mineral fillers such as titanium dioxide or alumina silicate, pigment dyes, ion and pH regulators and dry resistance resins such as carboxymethyl cellulose, form the base pulp for manufacturing paper with a consistency or concentration around 3% by weight with respect to the amount of water used with pH between 7 and 8.

Wet resistance resin based on polyamide-epichlorohydrin which is also strongly cationic and has the possibility to form covalent bonds similar to that indicated is subsequently added to the paper pulp and such bonds are formed with as many cellulose fibers are left with this option and it also forms such bonds with itself to form the polymer lattice necessary to give the paper the wet resistance level that is specified. This entire mass of cellulose fibers and chemical additives subsequently arrive from the machine head ink to the round shape where the layer of paper is formed after the pressing and drying processes.

After drying, the paper will move to the gluing area where it will be immersed in a tray that will contain a dilution of gluing agents based on polyvinyl alcohol (reference Airvol 103 manufactured by Air Products & Chemical) where 100 ml of aqueous dispersion of said combination of particles suitably functionalized to have the capacity to form covalent bonds with the oxygen atoms of the hydroxyl groups of the gluing agent will have been added for every 100 liters of gluing agent. The paper is subsequently dried and calendered until obtaining absolute moisture of the paper of 5%. The paper manufactured by these means is subsequently used for printing passports.

Example 5

Combination of Particles Consisted of 25% wt of $\beta\alpha$-$MnO_2$ Nanowires and 75% wt of $\beta$-$MnO_2$ Microrods as Security Markers Applied in the Coated Layer of Paper Intended for Printing Self-Adhesive Security Labels Material:
a knife coating machine which is supplied with a coating slip previously prepared according to the following specially indicated formula for a use of the coated paper in offset printing techniques for self-adhesive security labels, and an aqueous dispersion of a combination of particles consisted of 25% wt of $\beta\alpha$-$MnO_2$ nanowires with 50 nm in diameter and 3 μm in length and 75% wt of $\beta$-$MnO_2$ microrods with 4 μm in diameter and 8 μm in length where the composition present an absorption maximum at the frequency of 5.3 GHz and 1.4 GHz respectively.

Characteristics of the installations and materials used:

Mineral fillers: 80% calcium carbonate (Ref Albacar HO Slurry manufactured by Specialty Minerals) and 20% kaolin (reference Supragloss 95 manufactured by Imerys) to obtain 50 parts of the slip.

Synthetic binder: 10 parts butadiene styrene latex (reference Styronal D-517 manufactured by BASF).

Synthetic co-binder: 2 parts (reference Acronal 700 L manufactured by BASF).

Thickener: 1 part carboxymethyl cellulose.

Insolubilizing agent: 1 part (reference Basocoll OV manufactured by BASF).

Additives: 1 part sodium hydroxide.

Aqueous dispersion of particles as defined above: 1 part.

Water: The rest up to 100 parts.

Self-adhesive paper to be coated:
    Total grammage: 200 g/m$^2$
    Grammage of siliconized support: 82 g/m$^2$
    Grammage of adhesive: 20 g/m$^2$ Fibrous composition of the front side: 100% cellulose from mechanical pulp.

Conditions of the coating machine:
    Unwinder tension: 1000 N
    Winder tension: 120 N
    Winding hardness: 14%
    Drying tunnel temperature: 145° C.
    Machine speed: 150 m/min
    Residual moisture of the paper after drying: 6.5%

Characteristics of the coated paper:
    Total grammage: 220 g/m$^2$
    Grammage of coated layer: 20 g/m$^2$
    Bekk smoothness on the coated side: 200 sec
    Ash: 20%
    Opacity: 84%

Embodiment Method: Once the coating machine is started up to reach the established machine conditions, the reel of paper is placed on the unwinding shaft and the web of paper is distributed in the machine circuit, the coating slip is metered into the tray of the knife coater and the coating process begins according to the established machine conditions until finishing the reel. After the coating process, the reel of paper is calendered until reaching the smoothness established and is cut to the format necessary for the subsequent process for sheet or reel printing of the security labels.

Example 6

Combination of Particles Consisted of 10% wt of $Fe_3O_4$ Nanosheets and 90% wt of $CoZr_4(PO_4)_6$ Nanoparticles as Security Markers Applied in the Coated Layer of Paper Intended for Printing Postal Mail Stamps Material:

A filmpress coating machine which is supplied with a coating slip previously prepared according to the following formula such that the type and characteristics of the coating obtained is specially indicated for a use of the coated paper in gravure printing techniques for postal mail stamps, and an aqueous dispersion of a combination of particles consisted of 10% wt of $Fe_3O_4$ nanosheets with 100 nm in side length and 90% wt of $CoZr_4(PO_4)_6$ nanoparticles with 40 nm in diameter where the composition present an absorption maximum at the frequency of 10.24 GHz and 8.5 GHz respectively.

Characteristics of the Installations and Materials Used:

Mineral fillers: 50 parts kaolin (reference Supragloss 95 manufactured by Imerys).

Synthetic binder: 12 parts butadiene styrene latex (reference L-8000 manufactured by EOC Polymers).

Synthetic co-binder: 2 parts (reference Acronal 700 L manufactured by BASF).

Thickener: 1 part of carboxymethyl cellulose.

Insolubilizing agent: 1 part (reference Basocoll OV manufactured by BASF).

Additives: 1 part sodium hydroxide.

Aqueous dispersion of particles as defined above: 1 part.

Water: The rest up to 100 parts.

Paper support to be coated:
    Total grammage: 90 g/m$^2$
    Thickness: 120 microns
    Fibrous composition: 100% cellulose from mechanical pulp Conditions of the coating machine:
    Unwinder tension: 800 N
    Winder tension: 120 N
    Winding hardness: 14%
    Drying tunnel temperature: 150° C.
    Machine speed: 170 m/min
    Residual moisture of the paper after drying: 5.5%

Characteristics of the coated paper:
    Total grammage: 110 g/m$^2$
    Grammage of coated layer: 20 g/m$^2$
    Bekk smoothness on the coated side: 1800 sec
    Ash: 15%
    Opacity: 80%

Embodiment Method: Once the coating machine is started up to reach the established machine conditions, the reel of paper is placed on the unwinding shaft and the web of paper is distributed in the machine circuit, the coating slip is metered into the tray for supplying the cylinders in contact with the paper and the coating process begins according to the established machine conditions until finishing the reel. After the coating process, the reel of paper is calendered until reaching the established smoothness and is cut to the format necessary for the subsequent process for sheet or reel printing of postal mail stamps.

Example 7

Combination of Particles Consisted of 10% wt of $Fe_3O_4$ Nanosheets and 40% wt of $Fe_3O_4$ Nanoparticles and 50% Wt of $Ba_{0.9}Co_{0.2}Sm_{0.1}Fe_{16}O_{27}$ Particles as Security Markers Applied in the Gummed Layer of Paper Intended for Printing Gummed Tax Stamps or Security Labels Material:

A filmpress coating machine which is supplied with a slip of previously conditioned re-wettable gum which is specially indicated for the use of gummed paper for offset printing techniques for gummed tax stamps or security labels, the slip of re-wettable gum used that is based on polyvinyl acetate, reference A-4524 manufactured by Henkel Adhesives & Technologies, and an aqueous dispersion of a combination of particles consisted of 10% wt of $Fe_3O_4$ nanosheet with 100 nm in side length and 40% wt of $Fe_3O_4$ nanoparticles with 40 nm in diameter and 50% wt of $Ba_{0.9}CO_{0.2}Sm_{0.1}Fe_{16}O_{27}$ particles with platelet morphology with 3 μm in diameter and 0.25 μm in thickness where the composition present an absorption maximum at the frequency of 10.24 GHz, 8.2 GHz and 15 GHz respectively.

Characteristics of the Installations and Materials Used:

1 liter of aqueous dispersion of a combination of particles as defined above and 1400 grams of green food dye with reference Verde Carta DAM Líquido manufactured by Clariant previously prepared by mixing 1 part of the dye indicated with 3 parts water are added for every 1000 kg tank of gum slip.

Characteristics of the paper support to be gummed:
  Total grammage: 95 g/m²
  Thickness: 98 microns
  Fibrous composition: 100% cellulose from mechanical pulp Conditions of the coating machine:
  Unwinder tension: 800 N
  Winder tension: 120 N
  Winding hardness: 45%
  Drying tunnel temperature: 130° C.
  Machine speed: 140 m/min
  Residual moisture of the paper after drying: 5.5%

Characteristics of the gummed paper:
  Total grammage: 105 g/m²
  Grammage of coated layer: 10 g/m²
  Re-wettable gum adhesion: 25 gF/mm
  Ash: 10%
  Opacity: 80%

Embodiment Method: Once the coating machine used to apply the re-wettable gum is started up to reach the established machine conditions, the reel of paper is placed on the unwinding shaft and the web of paper is distributed in the machine circuit, the gum slip is metered into the tray for feeding the cylinders in contact with the paper and the gumming process begins according to the established machine conditions until finishing the reel. After the gumming process, the reel of paper is cut to the format necessary for the subsequent process for sheet or reel printing of the gummed tax stamps or security labels.

The invention claimed is:

1. A method for preparing or marking a security document or article, said method comprising incorporating in said security document or article a composition comprising a combination of at least two types of particles of inorganic oxide materials, where each of the at least two types of particles has a different size and morphology characterized in that variation in the size distribution is less than 20% of mean particle size, and where the inorganic oxide materials have at least one transition metal or one lanthanide element, and radiofrequency wave absorption properties characterized by an intensity and bandwidth specific for each oxide material.

2. A security article, document or element comprising a composition comprising a combination of at least two types of particles of inorganic oxide materials, where each of the at least two types of particles has a different size and morphology characterized in that variation in the size distribution is less than 20% of mean particle size, and where the inorganic oxide materials have at least one transition metal or one lanthanide element, and radiofrequency wave absorption properties characterized by an intensity and bandwidth specific for each oxide material.

3. The security article, document or element according to claim 2, where the at least two types of particles have the same chemical composition.

4. The security article, document or element according to claim 2, where the composition has at least two radiofrequency wave absorption bands at specific frequencies.

5. The security article, document or element according to claim 2, where the inorganic oxide materials have a crystalline structure.

6. The security article, document or element according to claim 2, where the inorganic oxide materials have a wurtzite, spinel, ferrite, garnet or perovskite-type structure.

7. The security article, document or element according to claim 2, where the particles, or the particle aggregate, have an average size between 1 and 45 μm.

8. The security article, document or element according to claim 2, selected from identification documents, bank notes, checks, stamps and stamped paper, labels and tickets.

9. The security article, document or element according to claim 2 selected from security paper, paper pulp, security threads, security fibers, security inks, watermarks, tactile effects, cellulose strips, planchettes, holograms, security dyes or substances, plastic films, polymer substrates.

10. A method for determining the authenticity of a security document, article or element according to claim 2, which comprises measuring the radiofrequency absorption of said security document, article or element to determine the presence of a composition comprising the combination of at least two types of particles of inorganic oxide materials, where each of the at least two types of particles has a different size and morphology, and where the inorganic oxide materials have at least one transition metal or one lanthanide element, and radio frequency wave absorption properties.

11. The method according to claim 10, which comprises:
  (a) irradiating the security document, article or element with radio frequency radiation; and
  (b) determining the absorption of the radiofrequency radiation crossing the security document or article.

12. The method according to claim 11, which comprises:
  (a) irradiating the security document, article or element with radiofrequency radiation;
  (b) measuring the intensity of the radiofrequency radiation after crossing the security document, article or element;
  (c) measuring the intensity of the radiofrequency radiation after crossing a free space region; and
  (d) comparing the intensity of the signals of steps (b) and (c) to determine the absorption of the radiofrequency radiation crossing the security document, article or element.

13. The method according to claim 11, where the radiofrequency radiation used to irradiate the security document, article or element has a frequency between 3 KHz and 300 GHz.

14. An apparatus for determining the authenticity of a security document, article or element according to claim 2, comprising:
- an radiofrequency radiation transmitting antenna (2),
- a first radiofrequency radiation signal receiving antenna (3),
- a second reference radiofrequency radiation receiving antenna (1),
- where the first and second receiving antennas (1, 3) are arranged on either side of the transmitting antenna (2) and where between the transmitting antenna (2) and the first receiving antenna (3) there are support (4) for supporting the document (5) to be analyzed such that when the document (5) is in said support (4) in the operating mode, the document (5) is placed between the transmitting antenna (2) and the first receiving antenna (3) and where the apparatus further has:
- calculating means (6),
- first signal reader (7) connected with the first receiving antenna (3) and suitable for delivering the value of the measured signal to the calculating means (6),
- second signal reader (8) connected with the second receiving antenna (1) and suitable for delivering the measured reference value to the calculating means (6),
- where the calculating means (6) have an output (9) and are adapted for determining if the difference of values between the value of the signal measured in the first receiving antenna (3) and the value of the reference signal measured in the second receiving antenna (1) is in a pre-established range, delivering said result in the output (9).

15. A chemical composition for preparing or document or article comprising the a combination of at least two types of particles of inorganic oxide materials, where each of the at least two types of particles has a different size and morphology characterized in that variation in the particle size distribution is less than 20% of mean particle size, and
- where the inorganic oxide materials have at least one lanthanide element, and radiofrequency wave absorption properties characterized by an intensity an bandwidth specific for each oxide material.

* * * * *